US010279120B2

(12) United States Patent
Holmqvist

(10) Patent No.: US 10,279,120 B2
(45) Date of Patent: May 7, 2019

(54) MEDICAMENT DELIVERY DEVICE AND METHOD OF ASSEMBLING THE SAME

(71) Applicant: Carebay Europe Ltd, Sliema (MT)

(72) Inventor: Anders Holmqvist, Värmdö (SE)

(73) Assignee: SHL MEDICAL AG, Zug (CH)

( * ) Notice: Subject to any disclaimer, the term of this patent is extended or adjusted under 35 U.S.C. 154(b) by 496 days.

(21) Appl. No.: 15/038,529

(22) PCT Filed: Nov. 20, 2014

(86) PCT No.: PCT/EP2014/075078
§ 371 (c)(1),
(2) Date: May 23, 2016

(87) PCT Pub. No.: WO2015/078756
PCT Pub. Date: Jun. 4, 2015

(65) Prior Publication Data
US 2016/0287805 A1    Oct. 6, 2016

(30) Foreign Application Priority Data
Nov. 26, 2013  (SE) ...................... 1351405

(51) Int. Cl.
A61M 5/315   (2006.01)
A61M 5/24    (2006.01)
(Continued)

(52) U.S. Cl.
CPC .......... A61M 5/31565 (2013.01); A61M 5/24 (2013.01); A61M 5/28 (2013.01);
(Continued)

(58) Field of Classification Search
CPC ............ A61M 5/31565; A61M 5/3271; A61M 5/3272; A61M 2005/3261; A61M 5/24;
(Continued)

(56) References Cited

U.S. PATENT DOCUMENTS 7,662,131 B2    2/2010  Rimlinger et al.
2008/0269692 A1*  10/2008  James ................. A61M 5/3202
                                                          604/198
2013/0060191 A1*  3/2013  Thorley ............. A61M 5/3234
                                                          604/110

FOREIGN PATENT DOCUMENTS

WO    2005/009519 A1    2/2005
WO    2007/047200 A1    4/2007
WO    2012/000837 A1    1/2012

OTHER PUBLICATIONS

EPO, Int'l Search Report in PCT/EP2014/075078, dated Feb. 16, 2015.

* cited by examiner

Primary Examiner — Imani N Hayman
Assistant Examiner — Tiffany Legette
(74) Attorney, Agent, or Firm — McDonnell Boehnen Hulbert & Berghoff LLP

(57) ABSTRACT

A device for injecting a medicament includes a housing for a medicament container assembly, and an activation member axially movable relative to the housing between extended and retracted positions with a gripping member. A movement guide mechanism includes a first guide, a second guide that has a locking portion, and a guide follower that slides along the first guide when the activation member moves from the extended position to the retracted position and that slides along the second guide when the activation member moves from the retracted position to the extended position. The gripping member engages the container assembly when the activation member is in the retracted position. The locking portion interacts with the guide follower when the activation member moves from the retracted position to the extended position to restrict movement of the activation
(Continued)

member. A method of assembling a delivery device is also disclosed.

18 Claims, 14 Drawing Sheets

(51) Int. Cl.
*A61M 5/28* (2006.01)
*A61M 5/32* (2006.01)
*A61M 5/31* (2006.01)

(52) U.S. Cl.
CPC ...... *A61M 5/3137* (2013.01); *A61M 5/31501* (2013.01); *A61M 5/3271* (2013.01); *A61M 5/3272* (2013.01); *A61M 2005/3142* (2013.01); *A61M 2005/3247* (2013.01); *A61M 2005/3261* (2013.01); *A61M 2207/00* (2013.01)

(58) Field of Classification Search
CPC ... A61M 5/28; A61M 5/3137; A61M 5/31501
See application file for complete search history.

MEDICAMENT DELIVERY DEVICE AND METHOD OF ASSEMBLING THE SAME

TECHNICAL FIELD

The present disclosure generally relates to a medical device and in particular to a disposable medicament delivery device and to a method of assembling such a device.

BACKGROUND

Parameters which normally are to be taken into account when designing to disposable medicament delivery devices include measures to render it difficult to reuse the device and measures to protect users from needle sticks, especially after medicament administration.

U.S. Pat. No. 7,662,131 B2 discloses a liquid-injection syringe assembly. The assembly comprises a body forming a reservoir for the liquid, the body being provided with a liquid-injection needle, a plunger mounted to be axially movable in the body between a ready position and an end-of-injection position, and a sheath in which the body is mounted to be axially movable between an active position in which the needle projects from a distal end of the sheath, and a protecting position in which the needle is retracted inside the sheath. The assembly also comprises means for axially securing the plunger and the sheath in a relative position of the plunger and the sheath serving firstly to position the body in its protecting position relative to the sheath and secondly to position the plunger in its end-of-injection position relative to the body. In order to obtain the protecting position the syringe body is biased by means of a spring, which resiliently urges the syringe body towards its protecting position within the sheath when the plunger has reached the end-of-injection position.

A disadvantage with the syringe assembly of U.S. Pat. No. 7,662,131 is that it seems as if the plunger flange may snap into the axial securing means upon assembly of the syringe assembly as the plunger is inserted into the sheath from the distal sheath end and must thus be moved past the axial securing means to obtain the ready position. This interlocking of the plunger flange and the axial securing means pre-medicament administration would render it impossible to administer a medicament. Moreover, assuming that the plunger may be set in the ready position and thus enabling medicament administration, the inwardly protruding retaining abutments may obstruct the path along which the spring is to extend, which may result in only partial spring extension post medicament administration leading to undesired needle exposure.

SUMMARY

In view of the above, a general object of the present disclosure is to provide a medicament delivery device and a method of assembling the same which at least mitigate the problems of the prior art.

Hence, according to a first aspect of the present disclosure there is provided a medicament delivery device for injection of a medicament, comprising: a housing arranged to receive a medicament container assembly; an activation member axially movable relative to the housing between an extended position and a retracted position to expel medicament from the medicament container assembly, which activation member comprises gripping means, and wherein the housing and the activation member comprise a movement guide mechanism comprising a first guide, a second guide which has a locking portion, and a guide follower, wherein the guide follower is arranged to slide along the first guide when the activation member is moved from the extended position to the retracted position for expelling medicament, wherein the gripping means is arranged to engage the medicament container assembly when the activation member is in the retracted position, and wherein the guide follower is arranged to slide along the second guide when the activation member is moved back from the retracted position to the extended position, and wherein the locking portion is arranged to interact with the guide follower when the activation member has been moved back from the retracted position to the extended position to restrict movement of the activation member relative to the housing.

An effect which may be obtainable hereby is needle protection after administration of the medicament by essentially fixating the needle within the housing. The risk of needle sticks post medicament administration can thus essentially be eliminated and reuse of the medicament delivery device is rendered more difficult. Axial displacement of the needle from its exposed position to a protected position within the housing may be obtained by movement of the activation member towards the extended position after the gripping means has engaged with the medicament container assembly. This movement may be provided by manual action or automatically depending on to the implementation of the medicament delivery device. The locking portion restricts movement of the activation member after the activation member has reached its extended position such that exposure of the needle can be prevented.

According to one embodiment the first guide merges with the second guide so as to enable shifting of the guide follower from the first guide to the second guide. The utilisation of the first guide for guiding the guide follower when the activation member is moved from the initial extended position to the retracted position, and the second guide for guiding the guide follower when the activation member is moved back to the extended position thus provides different guide paths for the guide follower. In particular, the first guide enables movement from the extended position to the retracted position, while the second guide does not.

According to one embodiment the first guide is a track and wherein an external sidewall of the track defines the second guide.

According to one embodiment the first guide extends parallel with the second guide.

According to one embodiment the gripping means is arranged at an internal surface of the activation member.

The medicament delivery device as claimed in any of the preceding claims, wherein the gripping means is arranged to engage a flange portion of the medicament container assembly. Thus, medicament container assemblies of syringe type, which may be provided with a distal end flange, may engage with the gripping means.

According to one embodiment the activation member has a distal end portion relative to the housing, wherein the gripping means is arranged at the distal end portion.

According to one embodiment the activation member has a proximal end portion relative to the housing, wherein the gripping means is arranged at the proximal end portion.

According to one embodiment the gripping means is arranged to engage a head member of the medicament container assembly. Thus, medicament container assemblies of cartridge type, which may lack a distal end flange, but which may be provided with a head portion with corresponding means for engagement with the gripping means, may engage with the gripping means.

According to one embodiment the housing comprises the first guide and the second guide and the activation member comprises the guide follower. Alternatively, the housing could comprise the guide follower and the activation member could comprise the first guide and the second guide.

According to one embodiment the guide follower is flexible to enable shifting of the guide follower from the first guide to the second guide. The guide follower may thereby be bent for shifting the guide follower from the first guide to the second guide.

According to one embodiment the second guide is arranged to bend the guide follower in a direction towards a centre axis of the housing.

According to one embodiment the housing has an end wall which has an opening and the activation member has a central rod arranged to move through the opening, wherein the end wall is arranged to interact with the guide follower to retain the central rod within the housing.

One embodiment comprises an actuation member arranged to bias the activation member towards the extended position.

According to a second aspect of the present disclosure there is provided a method of assembling a medicament delivery device according to the first aspect. The method comprises:

a) providing a housing blank and an activation member blank, each of the housing blank and the activation member blank being provided with fold lines,
b) folding the housing blank along its fold lines to form the housing,
c) inserting a medicament container assembly into the housing,
d) folding the activation member blank along its fold lines to form the activation member, and
e) inserting a portion of the activation member into the housing.

The medicament delivery device may thereby be manufactured in a simple manner from two components; the housing and the activation member.

According to one embodiment the fold lines of the housing blank define two legs of the housing, and wherein the fold lines of the activation member blank define two legs of the activation member.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

In this disclosure examples of the claimed single-use or disposable medicament delivery device will be provided. As presented herein, such medicament delivery devices may be adapted to be utilised together with medicament container assemblies of syringe type or, alternatively, medicament container assemblies of cartridge type. Some of the examples relate to medicament delivery devices that require manual action from a user to protect the needle post administration of a medicament. Other examples relate to medicament delivery devices that provide automatic means for needle protection post administration of a medicament.

Generally, the medicament devices presented herein have a housing arranged to receive a medicament container assembly and an activation member arranged to be moved axially relative to the housing so as to enable administration of a medicament. This movement is provided along a first guide when the activation member is moved from an extended position relative to the housing to a retracted position relative to the housing. When the activation member is moved back from its retracted position to the extended state, the movement is provided along a second guide. For this purpose, a guide follower is arranged to follow the first guide during drug administration and the second guide when the activation member is moved back to its extended position. The activation member has a gripping means arranged to engage the medicament container assembly when the activation member is in the retracted position such that the medicament container assembly may be moved axially within the housing to retract the needle into the housing. Furthermore, a locking portion prevents or at least restricts movement of the activation member towards its retracted position after it has obtained its extended position post medicament administration.

The words "distal end" and "proximal end" may be used in conjunction with any of the components of the medicament delivery device. In each case, "proximal end" refers to that end of the component which is the end of the component in the direction of medicament administration, and "distal end" refers to the opposite end.

Figure 1:
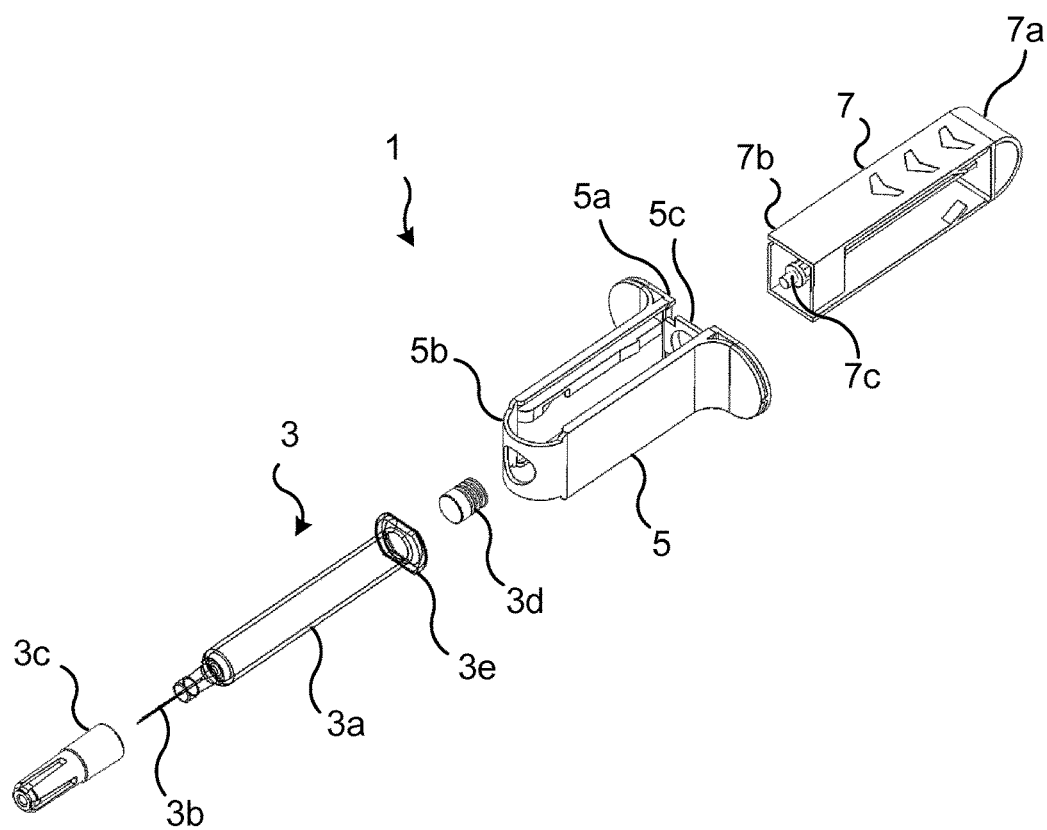
FIG. 1 depicts an exploded view of an example of a medicament delivery device.

FIG. 1 depicts an exploded view of an example of a medicament delivery device 1 and a medicament container assembly 3 of syringe type for use with medicament delivery device 1. The exemplified medicament delivery device 1 comprises a housing 5 and an activation member 7. The exemplified medicament container assembly 3 comprises a medicament container 3a having a flange portion 3e and arranged to hold a liquid medicament, a needle 3b arranged to expel medicament from the medicament container 3a, a needle shield 3c arranged to protect the needle prior to medicament administration and a stopper 3d arranged to seal the medicament container to 3a at its distal end and to slide within the medicament container 3a towards the proximal end thereof during medicament administration.

The housing 5 is arranged to receive the activation member 7 from a distal end 5a of the housing 5. The housing 5 has an end wall 5c with a central through-opening at the distal end 5a. The housing 5 is arranged to receive the medicament container assembly 3 such that a distal portion of the medicament container assembly 3 is arranged in the through-opening of the end wall 5c.

The activation member 7 has a distal end 7a and a proximal end 7b. The activation member 7 is arranged to move relative to the housing 5 from an extended position in which the activation member 7 protrudes from the housing 5 to a retracted position in which the majority of the activation member 7 is contained within the housing 5. The activation member 7 is arranged to interact with the medicament container assembly 3 when the activation member 7 is moved from the extended position to the retracted position. For this purpose the exemplified activation member 7 has a central rod 7c which interacts with the stopper 3d when the medicament container assembly 3 is arranged in the housing 5.

Figure 2A:
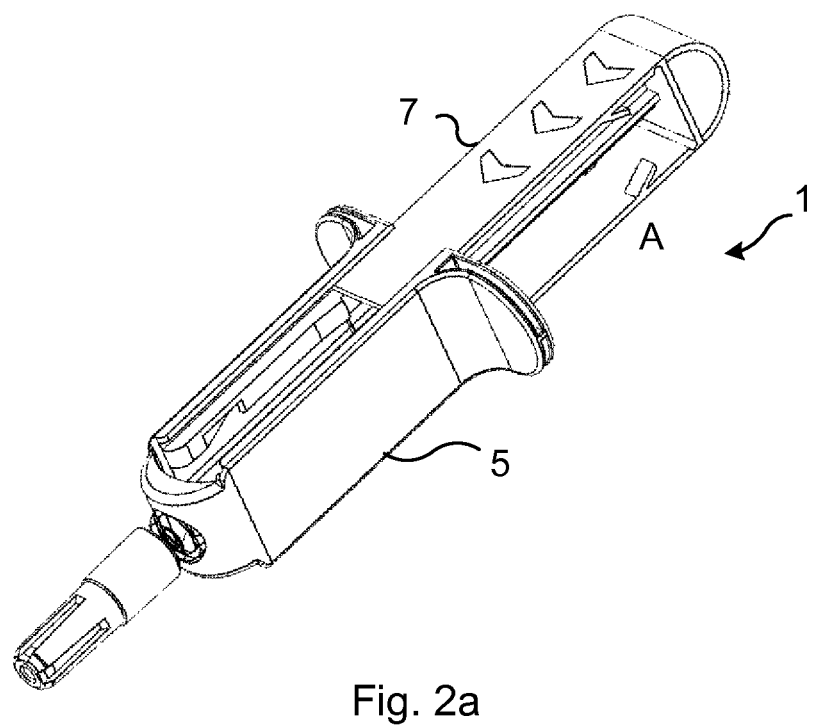
FIGS. 2a-c are perspective view of the medicament delivery device in FIG. 1, showing three steps of the medicament administration process.
Figure 2B:
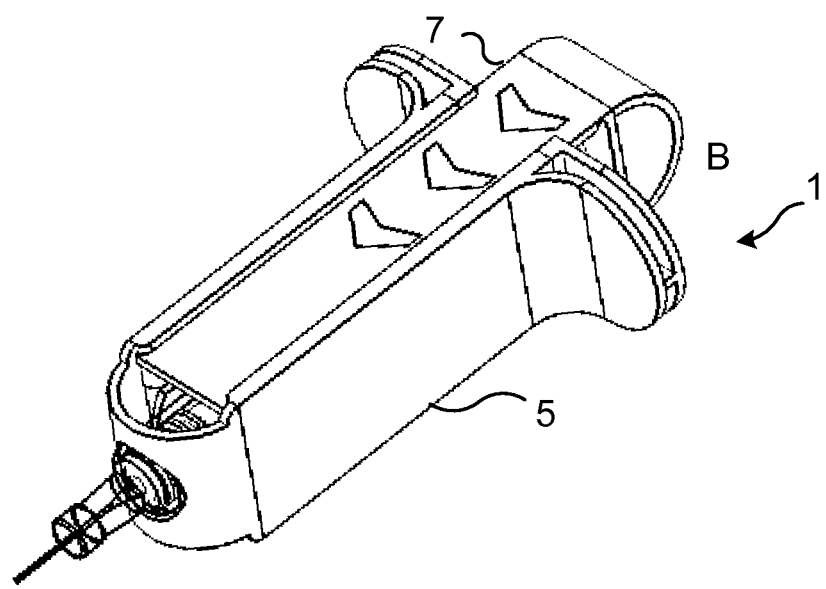
Figure 2C:
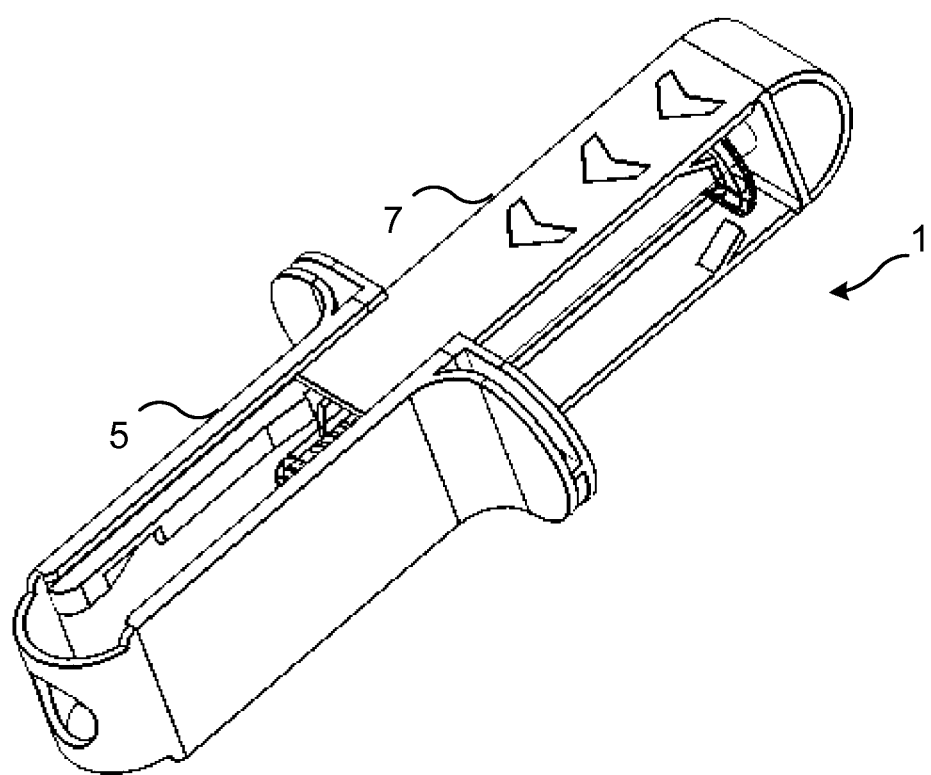

FIG. 2a shows a perspective view of the medicament delivery device 1 in FIG. 1 with the activation member 7 being in the extended position A prior to drug administration. In FIG. 2b the activation member 7 is in the retracted position B in which the content of the medicament container has been expelled from the medicament container 3a. FIG. 2c depicts the medicament delivery device 1 when the activation member 7 again is in the extended position A, post administration, wherein the medicament container assembly, comprising the needle, has been pulled within the housing 5.

Figure 3A:
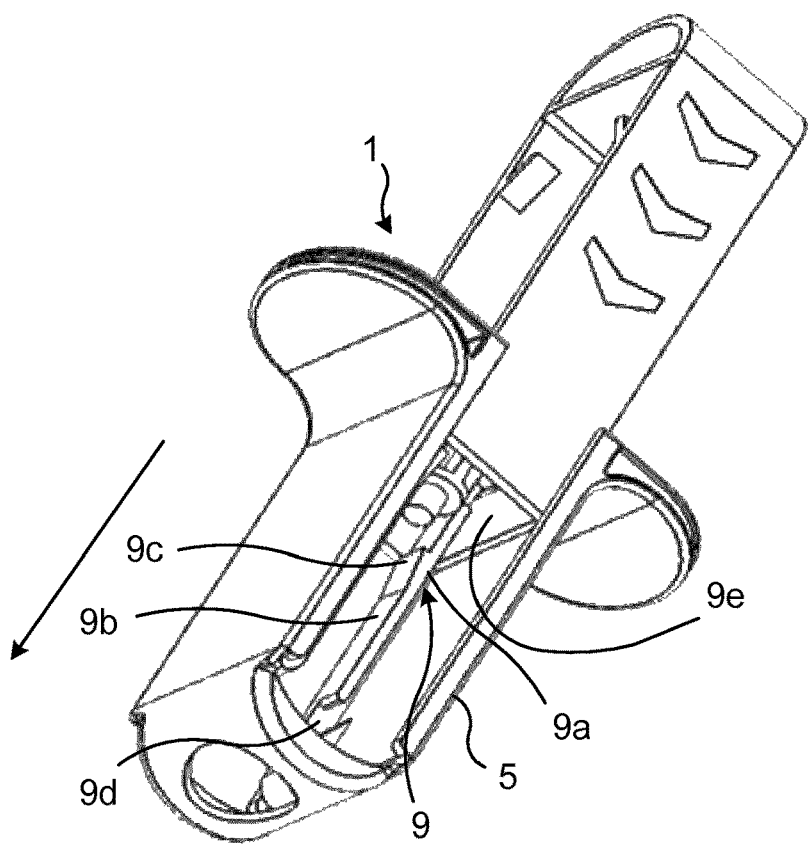
FIG. 3a is a perspective view of the medicament delivery device in FIG. 1.

The functioning of the medicament delivery device 1 will now be described in more detail with reference to FIGS. 3a-4c. FIG. 3a is a perspective view of the medicament delivery device 1. Although states of the medicament delivery device related to the administration of a medicament are shown in FIG. 3a, it should be noted that the medicament container assembly is not included in this figure in order to simplify the presentation.

The housing 5 and the activation member 7 comprise a movement guide mechanism 9 which guides movement of the activation member 7 relative to the housing 5, and which retains the activation member in the extended position A post administration. The movement guide mechanism 9 comprises a first guide 9a, a second guide 9b which has a locking portion 9c, a guide channel 9d between the first guide 9a and the second guide 9b, and a guide follower 9e. The first guide 9a and the second guide 9b extend parallel along a side wall of the housing 5.

According to the present example, the first guide 9a, the second guide 9b and its locking portion 9c, and the guide channel 9d are formed within the housing 5 and the guide follower 9e is formed within the activation member 7. Thus, in the present example, the housing 5 comprises the first guide 9a, the second guide 9b and its locking portion 9c, and the guide channel 9d and the activation member 7 comprises the guide follower 9e. It should however be noted that the converse arrangement is envisaged as an alternative realization. Thus, it is contemplated that the activation member could comprise the first guide, the second guide and its locking portion, and the guide channel and the housing could comprise the guide follower.

According to the present example, the guide follower 9e is flexible and may be bent in a direction away from the inner surface of the housing 5. The guide follower 9e may thus be flexible in a direction towards the centre axis of the housing 5. The exemplified guide follower 9e is defined by a flexible tongue at a proximal end of the activation member 7.

The first guide 9a may be a track in which the guide follower 9e is arranged to slide when the activation member 7 moves from the extended position A prior to being set into its retracted position B. When the activation member 7 is moved axially relative to the housing towards the retracted position B as shown by the arrow, the guide follower 9e slides along the first guide 9a towards the proximal end of the housing 5. The first guide 9a is connected with the second guide 9b at the proximal end of the first guide 9a via the guide channel 9d. The guide channel 9d extends from the first guide 9a to the second guide 9b and is arranged to enable shifting of the guide follower 9e from the first guide 9a to the second guide 9b. The guide channel 9d is thus arranged to direct the guide follower 9e from the first guide 9a to the second guide 9b. As a proximal end of the guide follower 9e enters the guide channel, it is bent away from the side wall of the housing 5, and as a distal end of the guide follower 9e passes a proximal end of the second guide 9b, the distal end of the guide follower snaps into alignment with the inner surface of the second guide 9b, allowing a return movement of the guide follower 9e along the second guide 9b.

According to the example in FIG. 3a, the guide channel 9d is inclined from the first guide 9a towards the second guide 9b in a direction from the distal end to the proximal end of the housing 5.

According to the example in FIG. 3a, the first guide 9a is closer to the side wall of the housing 5 than the second guide 9b. It is however contemplated that according to a variation of the movement guide mechanism, the second guide could be closer to the side wall of the housing than the first guide.

According to the present example, the second guide 9b is defined by the external surface of one of the side walls of the first guide 9a. The locking portion 9c of the second guide 9b protrudes from this side wall downstream of the guide channel 9d in a direction from the proximal end to the distal end of the housing 5. The locking portion 9c may be wedge-shaped and inclined in a direction from the proximal end to the distal end of the housing 5. Thereby the guide follower 9e is able to pass by the locking portion 9c when the activation member is moved from the retracted position back to the extended position by bending of the guide follower 9e in a direction away from the inner surface of the housing 5.

When the activation member 7 has been set into the extended position again the guide follower 9e will however not be able to move past the locking portion 9c due to the essentially right angle between the locking portion 9c and the side wall defining the second guide 9b, and also due to the longitudinal extent of the guide follower, which imparts a certain bending resistance, in the longitudinal direction, to the guide follower. The guide follower 9e will in this case not bend any further towards the centre axis of the housing 5 from the distal side of the locking portion 9c since there is no force acting on the guide follower in that direction.

The housing 5 and the activation member 7 may comprise two movement guide mechanisms. Thus, for example, the housing may comprise two sets of the first guide, the second guide with locking portion, the guide channel between the first guide and the second guide. The two sets are preferably diagonally disposed on the inner surface of the housing. The activation member may comprise two guide followers arranged to interact with a respective first guide, second guide, and guide channel. By providing additional movement guide mechanisms, a more robust medicament delivery device may be provided in terms of actuation of the activation member 7.

Figure 3B:
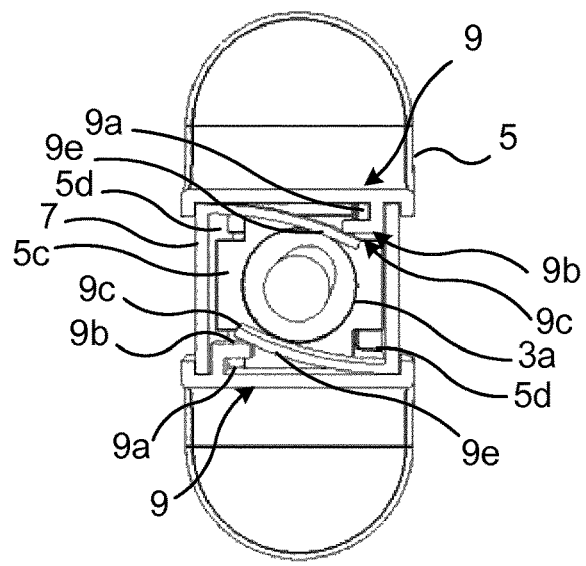
FIG. 3b is a cross section of the medicament delivery device in FIG. 1.

FIG. 3b shows a cross section of the medicament delivery device 1 post medicament administration when the activation member 7 is in a position between the retracted position and the extended position. The guide follower 9e has been shifted from the first guide 9a to the second guide 9b, and abuts the second guide 9b. The guide follower 9e is bent in a direction away from the inner surface of the housing 5, and when further actuated towards the extended position, will be further bent when passing the locking portion 9c. In the example in FIG. 3b, two sets of movement guide mechanisms 9 are depicted.

Figure 4A:
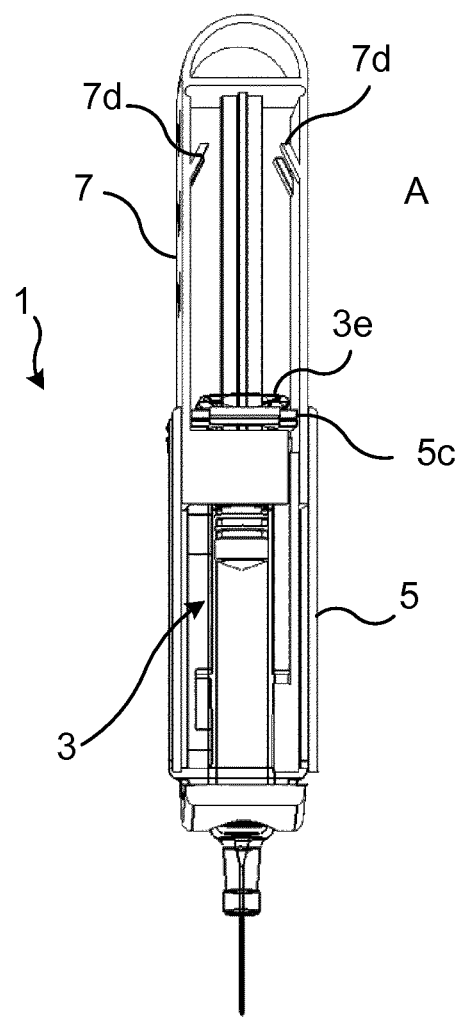
FIGS. 4a-c are longitudinal sections of the medicament delivery device in FIG. 1.
Figure 4B:
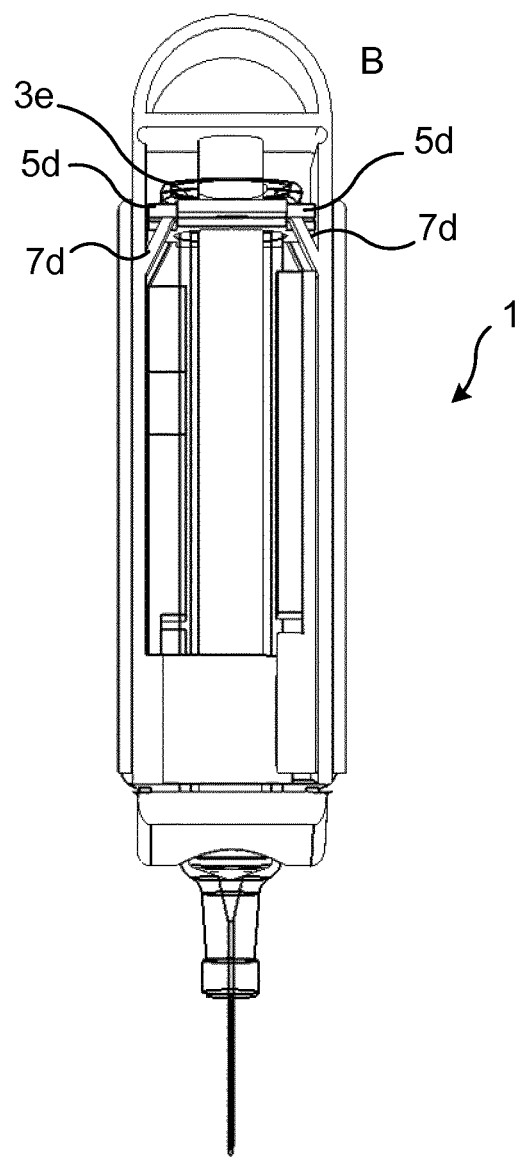
Figure 4C:
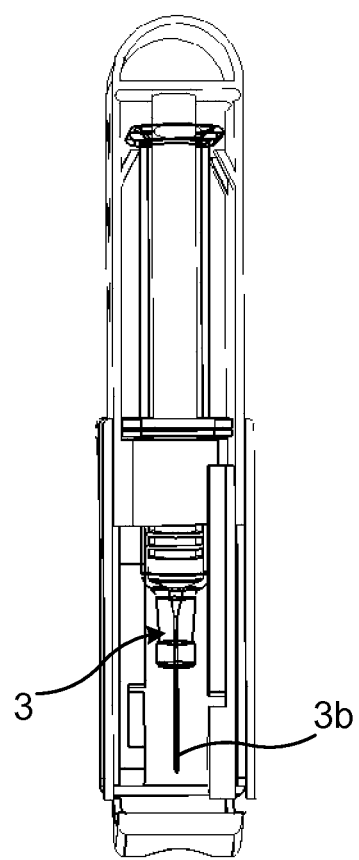

With reference to FIGS. 4a-c the gripping function of the medicament delivery device 1 will now be described in more detail. FIG. 4a depicts a side view of the medicament delivery device 1 when the activation member 7 is in the extended position A prior to medicament administration. The activation member 7 comprises gripping means 7d protruding from the inner surface of the activation member 7 and arranged to engage with the flange portion 3e of the medicament container assembly 3 when the activation member is in the retracted position.

As shown in FIG. 3b, the end wall 5c of the housing 5 has corner cutouts 5d. These corner cutouts 5d are aligned with the gripping means 7d enabling the gripping means 7d to pass through the corner cutouts 5d when the activation member 7 is moved to the retracted position. The corner cutouts 5d are dimensioned such that the flange portion 3e covers a portion of the corner cutouts 5d when the medicament container assembly 3 is arranged in the housing 5. The gripping means 7d protrude from the inner surface of the activation member such that they may interact with the flange portion 3e as the activation member 7 is moved from the extended position to the retracted position.

The exemplified gripping means 7d are flexible and can be bent towards the internal surface of the activation member 7. In particular, the gripping means 7d are arranged such that forces in a direction from the proximal end to the distal end of the activation member 7 applied to the gripping means 7d may resiliently bend the gripping means 7d towards the inner surface of the activation member 7. The gripping means 7d may thereby pass the flange portion 3e and the corner openings 5d when the activation member 7 is moved from the extended position to the retracted position. The gripping means 7d thus engages with the flange portion 3e when the activation member 7 is moved back from the retracted position to the extended position.

The medicament container assembly 3, including the needle, may thereby be pulled inside the housing 5.

Gripping means 7d may for example be an inclined tab, flange or tongue, with the inclination being defined in a direction from the proximal end to the distal end of the activation member 7.

In FIG. 4b, the medicament delivery device 1 is shown in the retracted position B, wherein the gripping means 7d have moved past the flange portion 3e and moved through the corner opening 5d. When the activation member 7 is moved back towards the extended position A, the gripping to means 7d engage with the flange portion, since they resist bending when the activation member 7 is moved towards the extended position. As depicted in FIG. 4c, the engagement of the gripping means 7d and the flange portion 3e results in that the medicament container assembly 3 and the needle 3b are drawn inside the housing 5. Needle sticks post medicament administration may thereby be avoided. Moreover, as elaborated hereabove, when the activation member 7 has been set in the extended position A post administration, the locking portion 9c prevents movement of the activation member 7 back to the retracted position B. Furthermore, the guide follower 9e is in this extended position A bent away from the inner wall of the housing 5 and may abut the end wall 5c of the housing 5 such that the activation member 7 is retained within the housing 5. In other words, it is not possible to remove the activation member 7 from the housing 5 after medicament administration, thereby reducing the risk of reuse of the medicament delivery device.

Figure 5A:
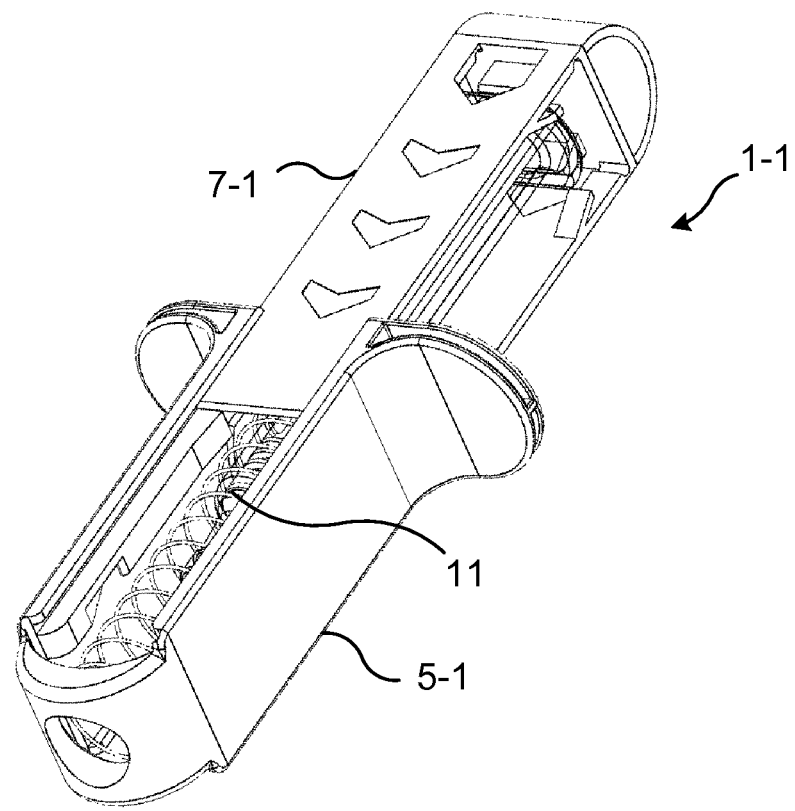
FIGS. 5a-d depict a variation of the medicament delivery device in FIG. 1.
Figure 5B:
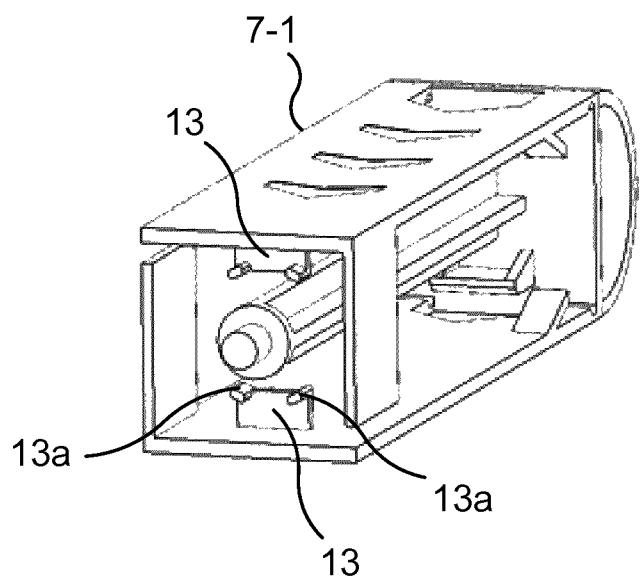

FIG. 5a depicts a variation of the medicament delivery device 1. Medicament delivery device 1-1 comprises an actuation member 11 arranged to bias activation member 7-1 towards the extended position A. The activation member 7-1 comprises supports 13, as shown in FIG. 5b, with which the actuation member 11 is arranged to interact. The actuation member 11 may be an energy accumulating member, for example a spring, such as a helical spring. The actuation member 11 extends between the inner proximate wall of the housing 5 and the supports 13. When the activation member 7-1 is in the extended position, the actuation member 11 exerts a smaller force to the supports 7-1a compared to when the activation member is in the retracted position biasing the activation member 7-1 towards the extended position.

The supports 13 may be protrusions, such as tabs, extending from the internal surface of the activation member 7-1. The supports 13 may further have position holders 13a arranged to restrict lateral movement of the actuation member 11.

Figure 5C:
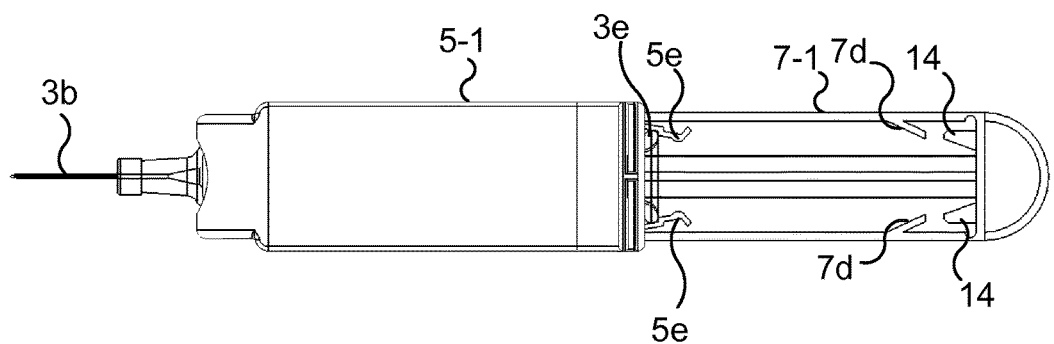
Figure 5D:
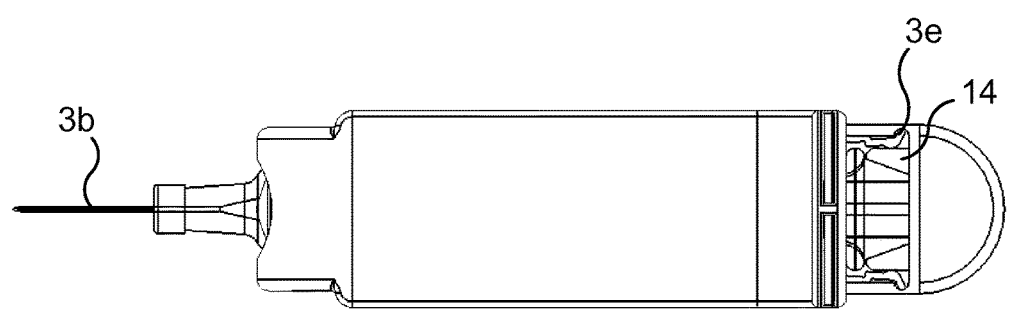

As shown in FIGS. 5c-d, the housing 5-1 has retention means 5e arranged to retain the medicament container 3a in position until the activation member 7-1 has obtained its retracted position. The activation member 7-1 has release means 14 arranged to interact with the retention means 5e when the activation member 7-1 has obtained its retracted position such that the medicament container may be released. When the gripping means 7d has engaged the flange portion 3e, the medicament container 3a may be moved within the housing such that when the activation member 7-1 is moved towards the extended position.

The retention means according to the present example are a pair of flexible tongues extending from the end wall 5c of the housing 5-1, arranged to interlock with the flange portion 3e such that the medicament container 3a may be maintained in position until the release means 14 bend the retention means 16 towards the activation member walls. The release means 14 may be protrusions extending from the distal end wall of the activation member 7-1.

The above-described design with retention means and release means is especially advantageous in the present example which includes actuation member 11 biasing the activation member 7-1 towards the extended position. When the activation member 7-1 is released, the central rod of the activation member 7-1 exerts a pulling force to the medicament container due to the activation member being biased, which would pull the medicament container 3a into the housing 5-1 prior to completion of the drug administration, if it was not retained by retention means 5e. The medicament container 3a is thus prevented from movement into the housing 5-1 in case the activation member 7-1 is released prior to reaching the retracted position. When the activation member 7-1 is moved towards the retracted position, interaction between the retention means 3e and the release means 14 releases the flange portion 3e and the gripping means 7d engages the flange portion 3e such that movement of the activation member 7-1 towards the extended position pulls the needle 3b into the housing 5-1.

Figure 6:
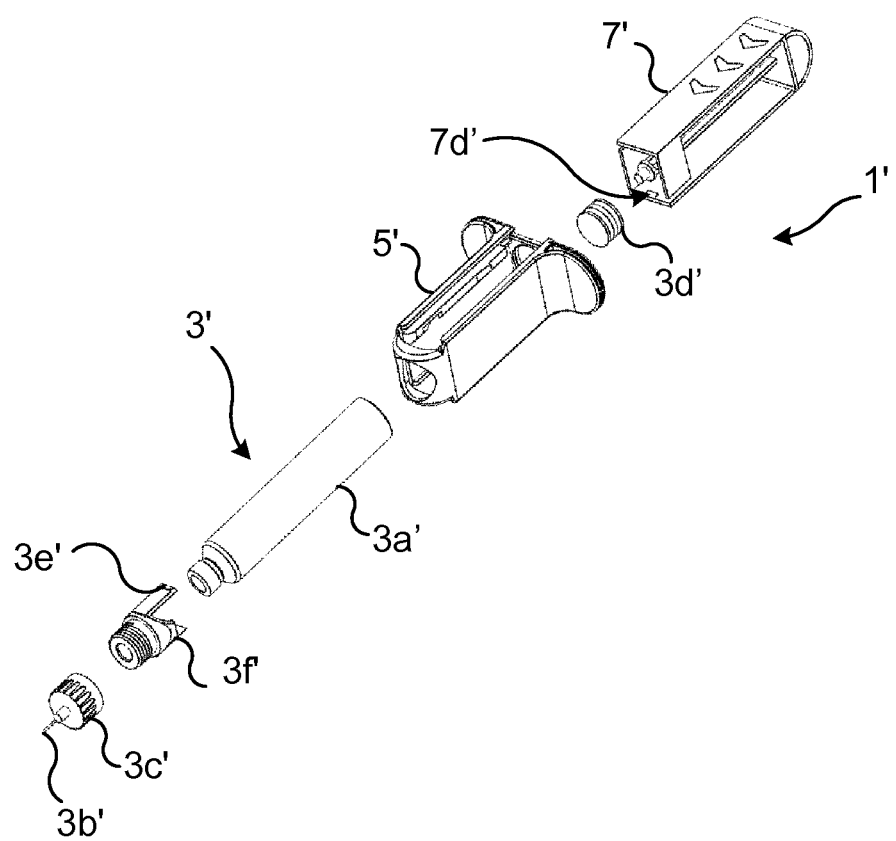
FIG. 6 is an exploded view of an example of a medicament delivery device.

FIG. 6 depicts another example of a medicament delivery device. Medicament delivery device 1' is similar to medicament delivery device 1. Medicament delivery device 1' is however adapted to accommodate a medicament container assembly 3' of cartridge type. The medicament delivery device 1' may comprise a housing 5' similar to the housing 5 described hereabove. In particular, the housing 5' comprises the same movement guide mechanism as medicament delivery device 1. The medicament delivery device 1' also comprises an activation member 7' which has gripping means 7d'.

The medicament container assembly 3' comprises a medicament container 3a', a head member 3f which may be threaded and which has engagement means 3e' arranged to engage with the gripping means 7d', a needle 3b' arranged to be assembled with the head member 3f, and a stopper 3d' with similar function as the stopper previously described. Since the structure of the housing 5' is similar to that already described, include any variation thereof, the housing 5 of medicament delivery device 1' will not be discussed any further herein.

The functioning of medicament delivery device 1' is similar to that of medicament delivery device 1 as shown in FIGS. 2a-c. The activation member 7' can thus obtain an extended position relative to the housing 5 and a retracted position relative to the housing 5. Moreover, the activation member 7' can be moved back from the retracted position to the extended position, wherein the gripping means 7d' which in the retracted position engages the engagement means 3e' of the head member 3f, pulls the medicament container assembly 3' into the housing 5' when the activation member is moved back to the extended position.

Figure 7:
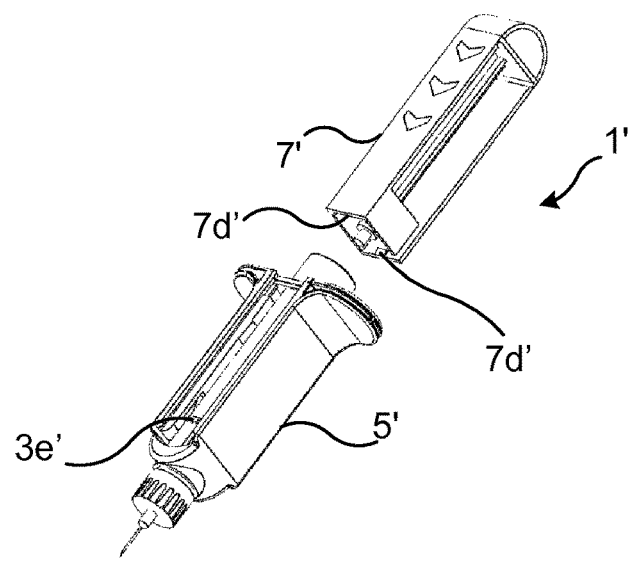
FIG. 7 is a perspective view of the medicament delivery device in FIG. 6.

As can be seen in FIG. 7, the gripping means 7d' may be wedge-shaped and it may be arranged at a proximal end of the activation member 7'. The engagement means 3e' of the head member 3f may also be wedge-shaped arranged oppositely compared to the gripping means 7d'. Thus the gripping means 7d' may be inclined in a direction from the proximal end to the distal end of the activation member 7', and the engagement means 3e' may be inclined in the opposite direction. The gripping means 7d' may thereby move to across the engagement means 3e' when the activation member is moved into the retracted position, wherein the gripping means 7d' and the engagement means 3e' engage such that movement of the activation member 7' towards the extended position axially displaces the head member 3f and places the entire medicament container assembly 3' within the housing 5' when the activation member 7' is moved back into the extended position.

Figure 8A:
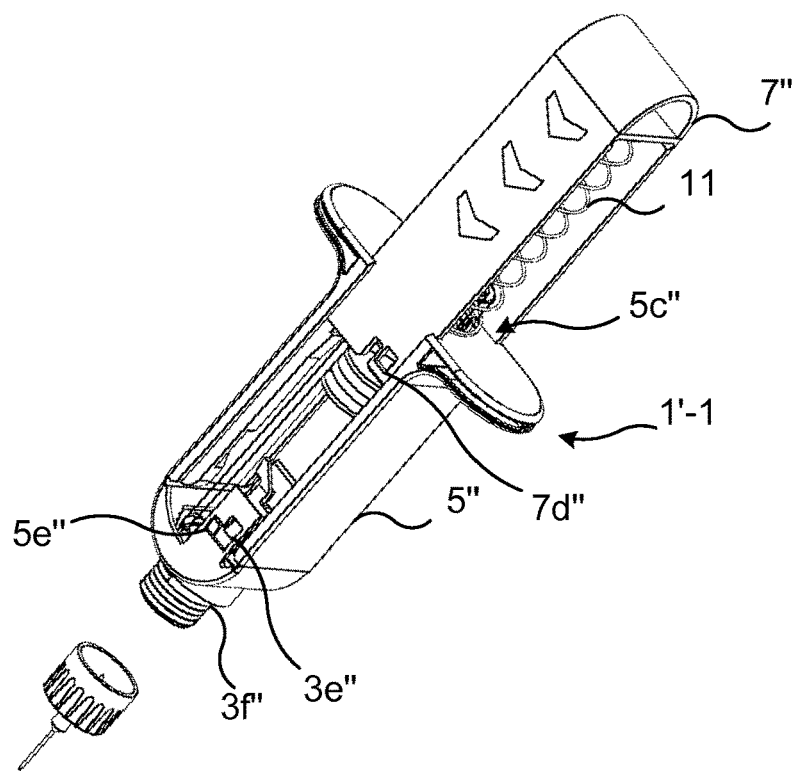
FIGS. 8a-c show a variation of the medicament delivery device in FIG. 6.
Figure 8B:
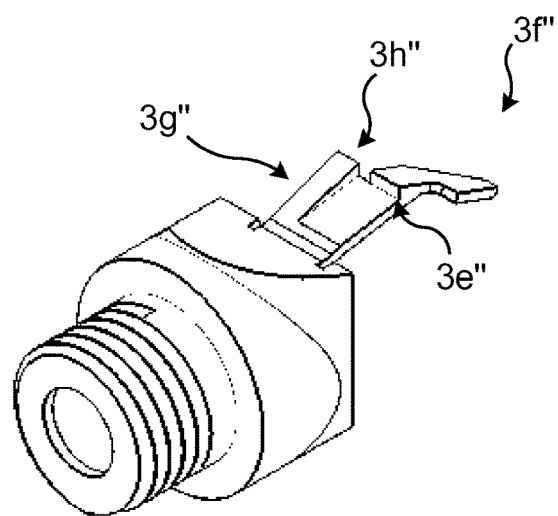
Figure 8C:
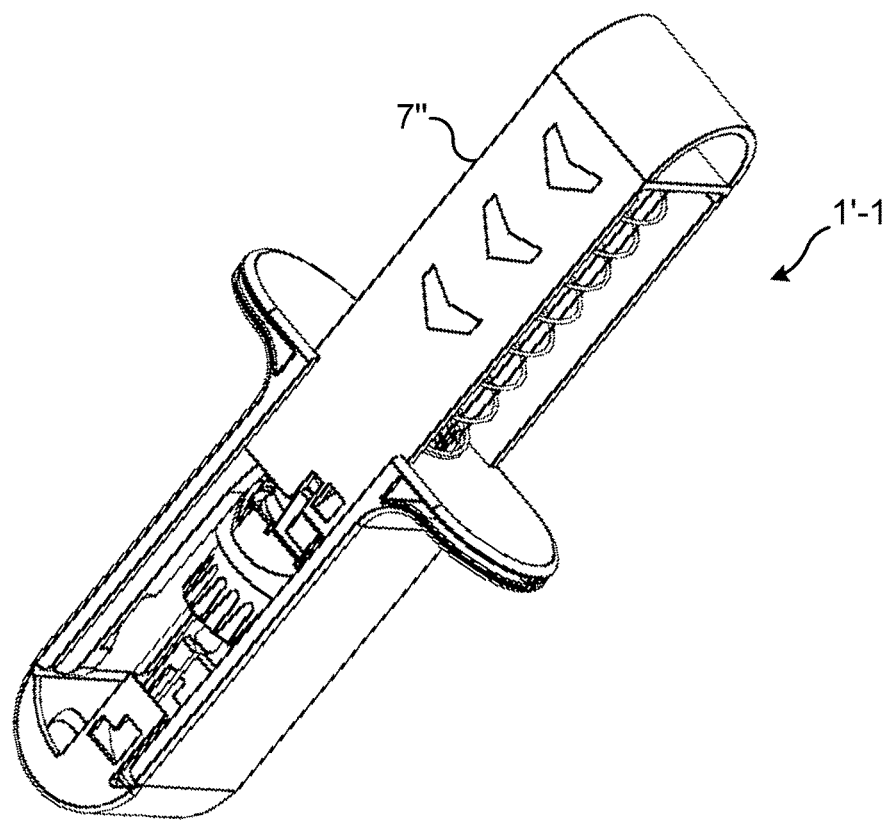

FIGS. 8a-c depict a variation of the medicament delivery device 1'. Medicament delivery device 1'-1 has a housing 5" and activation member 7" which differ from those previously described. It should be noted that the movement guide mechanism of this variation may be implemented according to any variation thereof previously presented.

The medicament delivery device 1'-1 comprises actuation means 11 arranged between the end wall 5c" of housing 5" and a distal inner end wall of the activation member 7". When the activation member 7" is in the extended position, the actuation member 11 exerts a smaller force to the end wall 5c compared to when the activation member 7" is in the retracted position in which the actuation member 11 biases the activation member 7-1 towards the extended position.

As shown in FIG. 8b, the housing 5'" has retention means arranged to retain the head member 3f" in position until the activation member 7" has obtained its retracted position. The retention means according to the present example is an opening 5e in the proximal end portion of the housing 5'". According to the example in FIGS. 8a-c, head member 3f' has engagement means 3e" which is a snap arranged to be snapped into the opening 5e". When snapped into the opening 5e" the engagement means 3e" prevents the head member 3f' from falling out from the proximal end opening of the housing 5".

Head member 3f' also has a snap portion 3h" arranged to be snapped into opening 5e" of the housing 5", and preventing the head member 3f' from movement into the housing 5" until the activation member 7" obtains its retracted position. The snap portion 3h" hence prevents axial movement, in a direction towards the distal end of the housing 5", of the head member 3f' prior to the activation member 7" obtains its retracted position. This is especially advantageous in the present example which includes the actuation member 11 biasing the activation member 7" towards the extended position. When the activation member 7" is released, the central rod of the activation member 7" exerts a pulling force to the medicament container due to the activation member being biased, which would pull the head member 3f" into the housing 5" prior to completion of the drug administration, if it was not retained by the snap portion 3h". The head member 3f' is thus prevented from movement into the housing 5" in case the activation member 7" is released prior to reaching the retracted position. When the activation member 7" is moved towards the retracted position, interaction with the activation member 7" releases the snap portion 3h" from the opening 5e" and the gripping means 7d" releases the engagement means 3e" from the housing 5" and interlocks with the engagement means 3e" such that movement of the activation member 7" towards the extended position pulls the head member 3f' into the housing 5".

FIG. 8b shows the head member 3f' which has a flexible tongue 3g" on which the engagement means 3e" is arranged. The engagement means 3e" has a lip arranged to interlock with the gripping means 7d" when the activation member 7" is in the retracted position. The gripping means 7d" is defined by the proximal wall of a cutout in the proximal end portion of the activation member 7". The gripping means 7d" is aligned with the engagement means 3e". The flexible tongue 3g" is also provided with the snap portion 3h". When the activation member 7" is moved towards the retracted position, it slides onto the flexible tongue 3g", wherein the flexible tongue 3g" is bent inwards such that the snap portion 3h" is released from the opening 5e" of the housing 5". Furthermore, the gripping means 7d" engages the engagement means 3e", which in combination with the released snap portion 3h", allows movement of the head member 3f" further into the housing 5". FIG. 8c illustrates the medicament delivery device 1'-1 when the activation member 7" is back in the extended position and the needle is contained within the housing 5".

Figure 9:
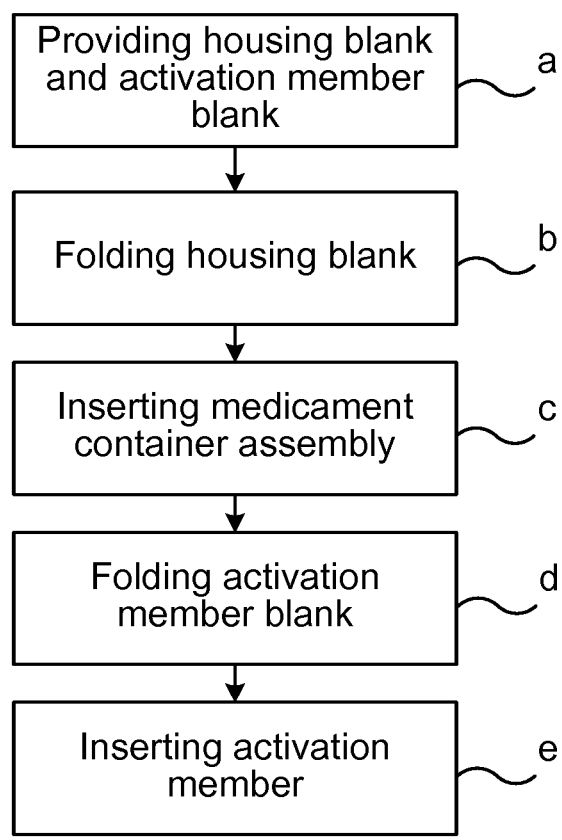
FIG. 9 depicts a flowchart of a method of assembling a medicament delivery device.
Figure 10A:
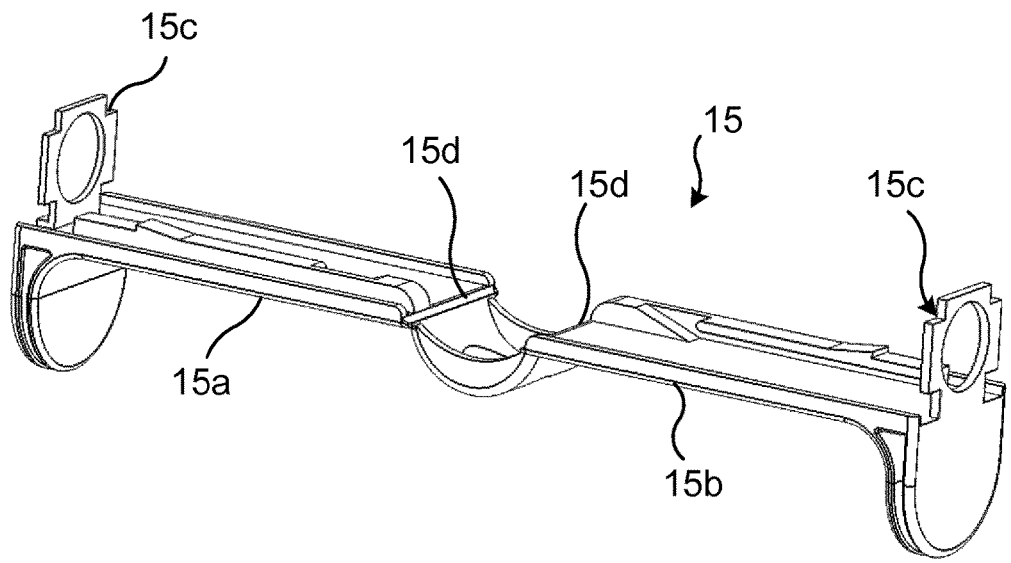
FIGS. 10a-b depict perspective views of a housing blank and an activation member blank, respectively, for assembling a medicament delivery device.
Figure 10B:
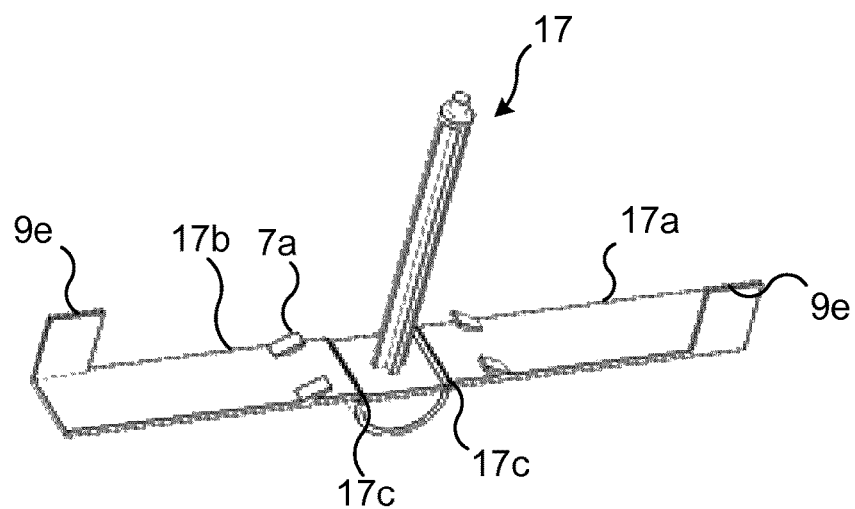

A method of assembling any of the medicament delivery devices presented herein will now be described with reference to FIG. 9 and FIGS. 10a-b.

In a step a) a housing blank 15 and an activation member blank 17 is provided. The housing blank 15 and the activation blank 17 may for example be created by means of injection moulding. Each of the housing blank 15 and the activation member blank 17 are provided with fold lines 15d, 17c. These fold lines 15d, 17c may for example be created by creasing.

The housing blank 15 comprises fold lines 15d which define two legs of a housing 5 created from the housing blank 15. The activation member 17 comprises fold lines 17 which define two legs of the activation member created from the activation member blank 17.

In a step b) the housing blank 15 is folded along its fold lines 15d to form the housing.

In a step c) a medicament container assembly is inserted into the housing created in step b). The medicament container assembly may be of syringe or cartridge type.

In a step d) the activation member blank 17 is folded along its fold lines 17c to form the activation member. It should here be noted that steps a)-d) do not necessarily have to be performed in the given order. The housing blank and the activation member may both prior to step c) be folded, in any order, before the medicament container assembly is inserted into the housing.

In a step e) a portion of the activation member is inserted into the housing such that the movement guide mechanism is set into its initial position, i.e. the guide followers are set to follow their respective first guide. Due to the resilient flexibility of the activation member and the guide followers it is possible to insert the activation member into the housing even though the end wall 5c obstructs a direct, longitudinal approach of the guide followers 9e into the first guides 9a.

Thanks to the interlocking structures of the housing and the activation member, and especially due to the blocking and locking function of the end wall 5c, after insertion of the activation member, it becomes impossible to detach the activation member from the housing without using undue force.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament delivery device for injection of a medicament, comprising: a housing arranged to receive a medicament container containing medicament; and an activation member axially movable relative to the housing between an extended position and a retracted position to expel the medicament from the medicament container, which activation member comprises a gripping device that is not directly engaged with the medicament container when the activation member is in the extended position; wherein the housing and activation member comprise a movement guide mechanism, comprising a first guide, a second guide that has a locking portion, and a guide follower; the guide follower slides along the first guide when the activation member moves from the extended position to the retracted position for expelling medicament; the gripping device resiliently bends to allow the gripping device to directly engage with the medicament container when the activation member is in moves from the retracted position to the extended position; the guide follower slides along the second guide when the activation member moves back from the retracted position to the extended position; the locking portion interacts with the guide follower when the activation member has moved back from the retracted position to the extended position to restrict movement of the activation member relative to the housing.

2. The medicament delivery device of claim 1, wherein the first guide merges with the second guide so as to enable shifting of the guide follower from the first guide to the second guide.

3. The medicament delivery device of claim 1, wherein the first guide is a track, and an external sidewall of the track defines the second guide.

4. The medicament delivery device of claim 1, wherein the first guide extends parallel to the second guide.

5. The medicament delivery device of claim 1, wherein the gripping device is arranged at an internal surface of the activation member.

6. The medicament delivery device of claim 1, wherein the gripping device engages a flange portion of the medicament container.

7. The medicament delivery device of claim 1, wherein the activation member has a distal end portion relative to the housing, and the gripping device is arranged at the distal end portion.

8. The medicament delivery device of claim 1, wherein the housing comprises the first guide and the second guide, and the activation member comprises the guide follower.

9. The medicament delivery device of claim 1, wherein the housing has an end wall with an opening; the activation member has a central rod arranged to move through the opening; and the end wall interacts with the guide follower to retain the central rod within the housing.

10. The medicament delivery device of claim 1, further comprising an actuation member arranged to bias the activation member toward the extended position.

11. The medicament delivery device of claim 1 where the housing has a distal end wall comprising a through-opening, where the end wall comprises overlapping distal portions of two legs of the housing.

12. The medicament delivery device of claim 1 where the gripping device is located at a distal end of the activation member and the guide follower is located at a proximal end.

13. The medicament delivery device of claim 1, wherein the activation member has a proximal end portion relative to the housing, and the gripping device is arranged at the proximal end portion.

14. The medicament delivery device of claim 13, wherein the gripping device engages a head member of the medicament container.

15. The medicament delivery device of claim 1, wherein the guide follower is flexible to enable shifting the guide follower from the first guide to the second guide.

16. The medicament delivery device of claim 15, wherein the second guide bends the guide follower toward a center axis of the housing.

17. A method of assembling a medicament delivery device according to claim 1, the method comprising:
 a) providing a housing blank and an activation member blank, each of the housing blank and the activation member blank being provided with fold lines;
 b) folding the housing blank along its fold lines to form the housing;
 c) inserting the medicament container into the housing;
 d) folding the activation member blank along its fold lines to form the activation member; and e) inserting a portion of the activation member into the housing.

18. The method of claim 17, wherein the fold lines of the housing blank define two legs of the housing, and the fold lines of the activation member blank define two legs of the activation member.

\* \* \* \* \*